United States Patent
Peru et al.

(10) Patent No.: US 10,591,412 B2
(45) Date of Patent: Mar. 17, 2020

(54) POLYMER SCREENING METHODS

(71) Applicant: Colgate-Palmolive Company, New York, NY (US)

(72) Inventors: Deborah Ann Peru, Lebanon, NJ (US); Rensl Dillon, Ewing, NJ (US); Shira Pilch, Highland Park, NJ (US); Venda Porter Maloney, Piscataway, NJ (US); Lin Fei, Kendall Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 20 days.

(21) Appl. No.: 15/328,762

(22) PCT Filed: Jul. 24, 2014

(86) PCT No.: PCT/US2014/048050
§ 371 (c)(1),
(2) Date: Jan. 24, 2017

(87) PCT Pub. No.: WO2016/014066
PCT Pub. Date: Jan. 28, 2016

(65) Prior Publication Data
US 2017/0212040 A1    Jul. 27, 2017

(51) Int. Cl.
| | | |
|---|---|---|
| *G01N 21/35* | (2014.01) |
| *G01N 21/84* | (2006.01) |
| *G01N 21/359* | (2014.01) |
| *G01N 21/17* | (2006.01) |

(52) U.S. Cl.
CPC ........... *G01N 21/35* (2013.01); *G01N 21/359* (2013.01); *G01N 21/8422* (2013.01); *G01N 2021/1748* (2013.01)

(58) Field of Classification Search
None
See application file for complete search history.

(56) References Cited

U.S. PATENT DOCUMENTS

| | | | |
|---|---|---|---|
| 8,895,929 B2 | 10/2014 | Gronlund et al. | |
| 2011/0024629 A1* | 2/2011 | Gronlund | A46B 15/0002 250/339.01 |
| 2012/0020899 A1* | 1/2012 | Zaidel | A61K 8/25 424/52 |

FOREIGN PATENT DOCUMENTS

| | | |
|---|---|---|
| RU | 2164350 | 3/2001 |
| WO | 2005/099404 | 10/2005 |
| WO | WO 2009/124310 | 10/2009 |
| WO | WO 2010/115041 | 10/2010 |

OTHER PUBLICATIONS

Barkvoll et al., 1988, "Studies on the interaction between sodium lauryl sulfate and hydroxyapatite using Fourier transformed infrared spectroscopy," Journal de Biologie Buceale, Societe Nouvelle de Publications Medicales et Dentaires 16(2):75-79.
International Search Report and Written Opinion in International Application No. PCT/US2014/048050, dated May 6, 2015.
Jones et al., "Compendium of Polymer Terminology and Nomenclature", Compendium of Polymer Terminology and Nomenclature—Purple Book, pp. 215-218(2008).

* cited by examiner

*Primary Examiner* — Edwin C Gunberg

(57) ABSTRACT

This application is directed to methods of assessing polymer deposition on dental surfaces using near infrared spectroscopy, providing a rapid and efficient method to screen for and identify optimal polymers for use in oral care formulations, (i) near infra red (IR) absorption of a dental substrate is measured in the absence of a polymer under test, and subsequently of the test sample comprising the dental substrate contacted with the test polymer. After washing or rinsing the test sample near IR of it is determined again (iii). The IR absorption of the test polymer itself is also measured (ii). Through the comparison of the three measurements (i), (ii), and (iii) the degree of deposition and retention of the test polymer on the test sample is determined.

11 Claims, No Drawings

POLYMER SCREENING METHODS

BACKGROUND

Polymers are commonly used in oral care products such as toothpaste, not only as viscosity modifiers, but also to inhibit biofilm and plaque formation, to enhance the delivery and effectiveness of active ingredients, and to alleviate conditions such as dry mouth (xerostoma).

The precise interactions between polymers and tooth surfaces can be unpredictable, particularly when the teeth are coated with saliva and/or biofilm, as there may be complex interactions between the polymer, the proteins in the saliva, the biofilm, other ingredients in the oral care formulation, and the tooth surface. Different types of polymers may have different functional groups, which can participate in hydrogen bonding or ionic bonding to facilitate deposition and retention of the polymer on the tooth surface, but which may also interact with proteins in the saliva, biofilm, and other ingredients in the oral care formulation.

While it may be possible to predict in general terms that a particular type of polymer would be useful for a particular application, it may be more difficult to select exactly which of the many variants of that polymer type would be optimal. For many polymers, there is a large choice of different brands or grades of polymers of produced from the polymerization of the same monomer, each having differences in molecular weight, degree of substitution and/or crosslinking, and other properties that could affect optimal deposition and retention on the tooth surface.

Measuring polymer deposition on saliva-coated hydroxylapatite (scHAP) disks using current methods requires that the discs be exposed to polymer, washed, then the polymer is removed, e.g., by solvent extraction, and subsequently quantified by high-performance liquid chromatography (HPLC). This process is indirect, time consuming and provides no information about potential active-substrate interactions. It is of course possible to make formulations comprising various test polymers and evaluate performance in vivo, but this is time consuming and expensive as an initial screening method. There is a need for an assay that can rapidly and efficiently assess and quantify polymer deposition and retention on dental surfaces in vitro in order to screen and identify optimal polymers for use in oral care products.

Near-infrared spectroscopy (NIRS) is a spectroscopic method that uses the near-infrared region of the electromagnetic spectrum (from about 700 nm to 2500 nm). It has been used in a variety of applications, but not to measure polymer deposition on dental surfaces or to screen polymers for use in oral care products.

BRIEF SUMMARY

The disclosure provides, in one embodiment, a novel method using near-infrared spectroscopy to assess and quantify the interaction of polymers, such as carboxymethyl cellulose (CMC) and polyvinylpyrrolidone (PAR), with dental substrates, such as hydroxylapatite (HAP) disks, dentin, bovine teeth etc. Polymer deposition on HAP is driven by the specific interactions between polymer and salivary proteins.

For example, the disclosure provides in a first embodiment, Method 1, a method of measuring polymer deposition on a dental substrate comprising:
a) measuring the near IR absorption of a dental substrate in the absence of test polymer;
b) measuring the near IR absorption of a test polymer;
c) obtaining a test sample by contacting a dental substrate with the test polymer or a formulation comprising the test polymer;
d) washing or rinsing the test sample;
e) measuring the near IR absorption of the test sample;
e) comparing the near IR absorption of (i) the dental substrate in the absence of test polymer, (ii) the test polymer, and (iii) the test sample, to determine the degree to which the test polymer is deposited and retained on the test sample.

For example, the invention provides:
1.1. Method 1 wherein the dental substrate is selected from mammalian tooth, e.g., human tooth or bovine tooth, dentin, hydroxylapatite, e.g., hydroxylapatite disks, dentures, dental trays and dental strips.
1.2. Method 1.1 wherein the dental substrate is a saliva-coated dental substrate.
1.3. Method 1.2 wherein the saliva-coated dental substrate is saliva-coated hydroxylapatite disks.
1.4. Any foregoing method wherein the test polymer is selected from carboxymethyl cellulose (CMC) and polyvinylpyrrolidone (PYP), e.g. cross-linked PVP or PVP-hydrogen peroxide complex.
1.5. Any foregoing method wherein the method is carried out entirely in vitro.
1.6. Any foregoing method wherein the method is carried out ex vivo.
1.7. Any foregoing method wherein steps d and e are repeated to assess retention of the test polymer.
1.8. Any foregoing method wherein the washing or rinsing is carried out using saline buffer solution.
1.9. Any foregoing method wherein the area between the absorption curve of the near IR absorption of the saliva-coated dental substrate in the absence of test polymer and the absorption curve of the near IR absorption of the test sample after washing or rinsing is correlated with the amount of test polymer deposited and retained on the test sample.
1.10. Any foregoing method wherein the absorption curve of the near IR absorption of the saliva-coated dental substrate in the absence of test polymer and the absorption curve of the near IR absorption of the test sample after washing or rinsing are scored using principal component analysis to generate scores quantifying the difference between the two, wherein the degree of difference correlates with the amount of test polymer deposited and retained on the test sample.
1.11. Any foregoing method wherein the method is repeated using different test polymers.
1.12. Any foregoing method wherein the method is repeated using different concentrations of test polymer.
1.13. Any foregoing method wherein the method is repeated in the presence and absence of different formulation ingredients to determine the effect of the ingredients on polymer binding.
1.14. Any foregoing method wherein the test sample is obtained by contacting a saliva-coated dental substrate with a formulation comprising the test polymer, wherein the formulation is a toothpaste formulation.
1.15. Any foregoing method wherein the method is used to screen for and identify optimal polymers for use in an oral care formulation, e.g., a toothpaste.
1.16. Any foregoing method wherein the near IR absorption is measured in the range of 700 to 2500 nm.
1.17. Any foregoing method wherein the near IR absorption is measured in the range of 2000 to 2500 nm.

1.18. Any foregoing method wherein a non-saliva coated substrate is substituted for a substrate.

The disclosure also provides an oral care product comprising a polymer selected using any of Method 1, et seq.

The disclosure also provides for use of a near IR spectrometer in any of the foregoing methods.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

DETAILED DESCRIPTION

By "Near IR absorption" meant absorption of light in the range of from about 700 nm to about 2500 nm. The absorption range of 2000-2500 nm is of particular interest, as that is the range where the unique fingerprints of the different polymers we have tested are typically expressed. The spectral data is evaluated using a combination of approaches. First, the spectral changes on the test sample, e.g., HAP disk after deposition are observed. Strong vibrations in the regions specific for polymer provide evidence that polymer adhesion is occurring. Tracking the area under the curve can be done as a means to quantify retention after one washing and two washings with saline buffer solution. In addition, factor analysis can be used to identify the spectral differences observed across the entire spectrum. The use of principal component analysis (PCA) generates scores for each test sample measured. These are semiquantitative values assigned to each spectrum that shows the difference among the spectra. PCA scores that are very different from the control (no polymer coating) are considered to have the most polymer presence.

Advantages over alternative methods—Data acquisition is very fast—less than a day Atomic Force Microscopy (AFM) and Scanning Electron Microscopy (SEM) need vacuum pressure and can take weeks to Obtain results; and the sample is tested in its native state; there is no need for sample preparation; one benefit of having a fast analytical technique is that microcontaminants can alter or destroy the polymer or change the properties of the polymer over time.

The molecular overtone and combination bands seen in the near IR are typically very broad, leading to complex spectra; it can be difficult to assign specific features to specific functional groups or components. The overall shape of the spectra can be viewed as a "fingerprint" of the particular substance, and the intensity of the spectra correlates with the degree of deposition. Multivariate (multiple variables) calibration techniques (e.g., principal components analysis, partial least squares, or artificial neural networks) may be employed to identify differences in the presence and absence of polymer and so to measure polymer deposition.

The method is quick and efficient. One of the unique aspects of the Near IR method is that the method requires no clean up of the instrument. The samples are measured in flat and optically clear borosilicate glass vials using a diffuser that reflects light back to the detector, making analysis time extremely rapid. Total analysis time is less than one minute (approximately 30-35 seconds).

As noted above, differences in specific brands or grades of the same type of polymer can affect the properties of the polymer in oral care formulations.

For example, Carboxymethyl cellulose (CMC) is a cellulose derivative with carboxymethyl groups ($—CH_2—COOH$) bound to some of the hydroxyl groups of the glucopyranose monomers that make up the cellulose backbone. It is often used as its sodium salt, sodium carboxymethyl cellulose. Different types and grades of this polymer may have different chain lengths leading to different molecular weights, different levels of substitution resulting in different proportions of carboxymethyl groups compared to hydroxyl groups, different clustering of carboyxymethyl groups, and different degrees of ionization and salt formation.

Polyvinylpyrrolidone (PVP) is a water-soluble polymer made from the monomer N-vinylpyrrolidone. As in the case of CMC, different types and grades of this polymer may have different chain lengths leading to different molecular weights and viscosities. PYP may also be cross-linked and/or complexed with other ingredients, particularly hydrogen peroxide, in various proportions. Both CMC and PVP are available in a variety of brands, types, and grades, each having somewhat different properties in oral care formulations.

One embodiment of the application is a method of measuring polymer deposition on a saliva-coated dental substrate comprising:

a. measuring the near IR absorption of a saliva-coated dental substrate in the absence of test polymer;

b. measuring the near IR absorption of a test polymer;

c. obtaining a test sample by contacting a saliva-coated dental substrate with the test polymer or a formulation comprising the test polymer;

d. washing or rinsing the test sample;

e. measuring the near IR absorption of the test sample;

f. comparing the near IR absorption of (i) the saliva-coated dental substrate in the absence of test polymer, (ii) the test polymer, and (iii) the test sample, to determine the degree of deposition and retention of the test polymer on the test sample.

In another embodiment of the method, the saliva-coated dental substrate is a saliva-coated substrate selected from mammalian tooth, e.g., human tooth or bovine tooth, dentin, and hydroxylapatite.

In another embodiment of the method, the saliva-coated dental substrate is a saliva-coated hydroxylapatite disk.

In another embodiment of the method, the test polymer is selected from carboxymethyl cellulose (CMC) and polyvinylpyrrolidone (PVP).

In another embodiment of the method, the method is carried out entirely in vitro.

In another embodiment of the method, steps d and e are repeated to assess retention of the test polymer following washing or rinsing.

In another embodiment of the method, the washing or rinsing is carried out using saline buffer solution.

In another embodiment of the method, the area between the absorption curve of the near IR absorption of the saliva-coated dental substrate in the absence of test polymer and the absorption curve of the near IR absorption of the test sample after washing or rinsing is correlated with the amount of test polymer deposited and retained on the test sample.

In another embodiment of the method, the method is repeated using different concentrations of test polymer.

In another embodiment of the method, the method is repeated in the presence and absence of dentifrice ingredients to determine the effect of the dentifrice ingredients on polymer binding.

In another embodiment of the method, the dentifrice ingredients are selected from the group consisting of abrasives, amino acids, anti-bacterial agents, anti-plaque agents, breath freshening agents, colorants, desensitizing agents, fluoride ion source, stannous ion source, tartar control agents, whitening agents, zinc salts and combinations thereof.

The method of any foregoing claim wherein the dentifrice ingredients are whitening agents selected from the group consisting of peroxides, hydrogen peroxide, urea peroxide, high cleaning silica, blue pigments, blue dyes, chlorophyll compounds and combinations thereof.

The method of any foregoing claim wherein the method is repeated using different test polymers and further comprises the steps of:
  g. comparing the degree of deposition and retention of the test polymer against the degree of deposition and retention of the different test polymer; and
  h. selecting the test polymer from step g. with the greater degree of deposition and retention for use in a method of making dentifrice composition.

The method of any foregoing claim wherein the near IR absorption is measured in the range of 700 to 2500 nm.

The method of any foregoing claim wherein the near IR absorption is measured in the range of 2000 to 2500 nm.

Embodiments of the present invention are further described in the following examples. The examples are merely illustrative and do not in any way limit the scope of the invention as described and claimed.

EXAMPLES

Near IR Instrumentation Setup: The FOSS XDS Near IR instrument with Rapid Content Accessory (RCA) is used for all measurements. The spectra are collected from 400 nm to 2500 nm with 0.5 nm spacing between wavelengths. Reference standardization is employed, which involves using a certified 80% reference standard every 2 weeks to correct for y axis changes. The NIST traceable Standard Reference Material (SRM) 1920a is used every 2 weeks to correct for any x axis changes. Each sample measured is an average of 32 scans collected over a 20 second measurement interval.

In one embodiment of the invention, the spectra are collected over the range of from 2000 nm to 2500 nm. This range allows for better S/N (signal to noise) ratio and detection of lower concentrations of polymer.

In one embodiment of the invention, the concentration of the sample being detected can range from 100 ppm (0.0001% by weight=1 ppm) to 20,000 ppm. Other concentration ranges suitable for testing include 100 ppm to 10,000 ppm, 100 ppm to 1,000 ppm, and 100 to 500 ppm (concentrations higher than 10,000 to 20,000 can overwhelm the near IR data collection and is generally not suitable for use).

Performance qualification of the instrument is performed daily and consists of running an instrument performance test which measures both instrument noise and peak to peak band resolution. Reference scans using the internal reference standard are performed for each measurement. Samples are measured by placing the HAP disk directly on the sapphire lens and using the centering iris to center the disk in the center of measurement window. Spectral measurements were taken and saved three times without moving the sample. The process was repeated on the other side of the HAP disk.

Spectra of all raw materials are also measured and used to characterize the NIR fingerprint. The polymer powder is placed into a glass vial up to about 1 cm depth. The spectrum is taken in the same way as described above. Polymer solutions with and without sorbitol are also measured in order to evaluate interference of sorbitol in the measurement of CMC. Owing to a direct interference due to sorbitol in measuring CMC, all further Near IR experiments were conducted in NaCl solutions alone.

The spectra of several polymer solutions of different concentrations are also measured. The polymer solutions are put into the glass vial up to about 5 mm depth. A 316 stainless steel diffuser (2 mm effective pathlength) was then immersed into the solution to facilitate reflectance of the NIR light back to the detector. The space between the plate and the bottom of vial was checked to ensure no bubbles were trapped. The spectra are taken in the same way as described above.

High molecular weight (HMW) CMC refers to CMC with a number average molecular weight ranging from 400,000 to 1,000,000. Medium molecular weight (MMW) CMC refers to CMC with a number average molecular weight ranging from 150,000 to less than 400,000. Low molecular weight (LMW) CMC refers to CMC with a number average molecular weight ranging from 1,000 to less than 150,000.

CMC binding assessment: A bar plot of showing the area of polymer vibrational band after deposition on saliva coated HAP disks revealed the following areas under the curve (AUC) from the near IR spectra.

|  | Low MW CMC | Medium MW CMC | High MW CMC |
| --- | --- | --- | --- |
| 0.05% (no rinse) | 0.28 | 0.22 | 0.25 |
| 0.6% (no rinse) | 0.38 | 0.24 | 0.34 |
| 1% (no rinse) | 0.42 | 0.37 | 0.53 |

Both high and low molecular weight CMC show preferential binding to saliva coated HAP, compared to medium molecular weight CMC. The enhanced surface deposition is consistent with the enhancement in bioadhesion. CMC is one of the mucoadhesive polymers being investigated for use in products to treat dry mouth technology. Initial consumer testing shows that the dry mouth prototype product exhibits superior mouth moisture retention comparing to a regular dentifrice.

CMC data exemplifies the unique nature of the test technique in being able to distinguish not only between polymers, but also different types of polymers, e.g. surprising that HMW CMC and LMW CMC were better than MMW CMC for deposition.

PVP binding assessment: A series of proprietary PVP structures including cross linked PVP are screened using the same Near IR method after washing the substrate once with a polymer.

The Near IR spectrum provides a quantiative measure to track presence of polymer. Factor analysis (principal component analysis (PCA)) measures spectral differences among samples measured after one washing. The PCA scores plot clusters samples that are similar in fingerprint. The samples farthest away from the control most likely have the most polymer deposited on the surface. The PCA scores listed below represent 97% of the spectral variability between the samples.

| Polymer | PCA score |
|---|---|
| Alkylated PVP (Ganex ® V-216) | 0.40 |
| Crosslinked PVP (polyplasdone) | 0.35 |
| PVP-Maleic Acid (P139) | 0.31 |
| P(VP/HEA-PA) P 125 | 0.27 |
| Alkylated PVP (Ganex ® V-904) | 0.24 |
| Plasdone PVP K30 | 0.13 |
| Solvent wash (no polymer) | 0.05 |

A test of PVP treated samples revealed a p index of 0.07 indicating a close relationship between confidence intervals and significance tests. These Near IR methods are thus capable of finding PYP polymers that have the most binding potential to saliva coated surfaces and that show the most tenacious binding affinity with post washing. PYP polymers can be functionalized with or entrap whitening materials such as peroxide or other chemicals that deliver surface whitening benefits.

As those skilled in the art will appreciate, numerous changes and modifications may be made to the embodiments described herein without departing from the spirit of the invention. It is intended that all such variations fall within the scope of the appended claims.

What is claimed is:

1. A method of measuring polymer deposition on a saliva-coated dental substrate comprising:
   (a) measuring the near IR absorption of a saliva-coated dental substrate in the absence of test polymer;
   (b) measuring the near IR absorption of a test polymer;
   (c) obtaining a test sample by contacting a saliva-coated dental substrate with the test polymer or a formulation comprising the test polymer, wherein the test polymer is selected from carboxymethyl cellulose (CMC) and polyvinylpyrrolidone (PVP);
   (d) washing or rinsing the test sample;
   (e) measuring the near IR absorption of the test sample;
   (f) comparing the near IR absorption of (i) the saliva-coated dental substrate in the absence of test polymer, (ii) the test polymer, and (iii) the test sample, to determine the degree of deposition and retention of the test polymer on the test sample, wherein the near IR absorption is measured in the range of 2000 to 2500 nm; and
   (g) identifying a test polymer for use in an oral care formulation based on the detection of CMC or PVP when the near IR absorption is measured in the range of 2000 to 2500 nm.

2. The method of claim 1 wherein the saliva-coated dental substrate is a substrate selected from human tooth or bovine tooth, dentin, and hydroxylapatite.

3. The method of claim 1 wherein the saliva-coated dental substrate is a saliva-coated hydroxylapatite disk.

4. The method of claim 1 wherein the method is carried out in vitro or ex vivo.

5. The method of claim 1 wherein steps d and e are repeated to assess retention of the test polymer following washing or rinsing.

6. The method of claim 1 wherein the area between the absorption curve of the near IR absorption of the saliva-coated dental substrate in the absence of test polymer and the absorption curve of the near IR absorption of the test sample after washing or rinsing is correlated with the amount of test polymer deposited and retained on the test sample.

7. The method of claim 1 wherein the method is repeated using different concentrations of test polymer.

8. The method of claim 1 wherein the method is repeated in the presence and absence of dentifrice ingredients to determine the effect of the dentifrice ingredients on polymer binding.

9. The method of claim 1 wherein the dentifrice ingredients are selected from the group consisting of abrasives, amino acids, anti-bacterial agents, anti-plaque agents, breath freshening agents, colorants, desensitizing agents, fluoride ion source, stannous ion source, tartar control agents, whitening agents, zinc salts and combinations thereof.

10. The method of claim 1 wherein the dentifrice ingredients are whitening agents selected from the group consisting of peroxides, hydrogen peroxide, urea peroxide, high cleaning silica, blue pigments, blue dyes, chlorophyll compounds and combinations thereof.

11. The method of claim 1 wherein the method is repeated using different test polymers and further comprises the steps of:
   (g) comparing the degree of deposition and retention of the test polymer against the degree of deposition and retention of the different test polymer; and
   (h) selecting the test polymer from step g. with the greater degree of deposition and retention for use in a method of making dentifrice composition.

* * * * *